United States Patent [19]

Sandford

[11] 4,429,121

[45] Jan. 31, 1984

[54] CLARIFIED TAMARIND KERNEL POWDER

[75] Inventor: Paul A. Sandford, Del Mar, Calif.

[73] Assignee: Merck & Co., Inc., Rahway, N.J.

[21] Appl. No.: 330,627

[22] Filed: Dec. 14, 1981

Related U.S. Application Data

[63] Continuation of Ser. No. 151,495, May 19, 1980, abandoned.

[51] Int. Cl.³ .................... A61K 35/78; C08B 37/00
[52] U.S. Cl. .................... 536/123; 424/195; 536/114; 536/124
[58] Field of Search .................. 536/114, 1, 123, 124; 424/195; 260/236.5

Primary Examiner—Stanley J. Friedman
Attorney, Agent, or Firm—Gabriel Lopez; Hesna J. Pfeiffer

[57] ABSTRACT

A clarified tamarind kernel powder is produced by treating tamarind kernel powder with a strong base, followed by neutralization and isolation.

10 Claims, No Drawings

CLARIFIED TAMARIND KERNEL POWDER

This is a continuation, of application Ser. No. 151,495, filed May 19, 1980, now abandoned.

BACKGROUND OF THE INVENTION

Tamarind kernel powder (TKP) has been employed in a large variety of industrial applications; most notably as a sizing for textiles. A limitation with this product has been that it is cloudy, thus precluding certain applications where clarity is essential, e.g., as a replacer for pectin. Attempts in the past to produce a more useful product have included methods of extracting either the polysaccharide or the insolubles from the crude TKP. These methods have included filtration, centrifugation, alcohol extraction, air classification, etc.

U.S. Pat. No. 3,287,350 teaches the art of purifying TKP to obtain tamarind seed jellose (TSJ), the polysaccharide constituent of TKP, also known as gellose, polyose, and pectin. The process requires bleaching of the coarsely ground tamarind seed kernels which are then dispersed in a 25-fold amount of water. After injection of steam, the solution is filtered and the TSJ precipitated by using a sulfate and alcohol. U.S. Pat. No. 3,399,189 teaches the art of making a cold-water soluble product from TKP by extracting the polysaccharide from tamarind seed kernels with isopropanol at 80° C., the polysaccharide then being dispersed in a 25- to 35-fold amount of water. Injection of steam and subsequent filtration yield a cold-water-soluble product which is recovered from solution by roll drying or precipitation with an organic solvent.

SUMMARY OF THE INVENTION

It has now been found that treatment of TKP with an aqueous alkali solution of pH 10–14 produces a product of greatly improved clarity. The dried (less than 20% of $H_2O$) and milled product also exhibits enhanced solubility in cold water when compared to TKP. The clarified tamarind kernel powder contains about 2–10% protein; a 0.25% solution in deionized water (D.I.) has a transmittance of about 70–80% at 485 nm.

DETAILED DESCRIPTION

Tamarind kernel powder (TKP) is a commercially available product obtained by husking and milling the seed kernels of the tree, *Tamarindus indica* (Linn). TKP includes all of the constituents found in the tamarind seed kernel: polysaccharide (composed of uronic acid and the neutral sugars arabinose, xylose, mannose, glucose, and galactose), protein, and other cellular debris from the tamarind kernel seed. TKP is crude and insoluble in cold water (in the range of 5°–35° C.).

In the process of this invention, TKP is mixed for about two hours with an alkali aqueous solution (preferably a strong alkali such as 50% NaOH) to form an aqueous slurry. The amount of alkali used is such that the pH of the slurry is in the range pH 10–14. A pH of about 13 is preferred. The slurry is diluted with five volumes of water and stirred for another two hours. The diluted slurry is then, optionally, neutralized with concentrated acid (e.g., HCl) and the polysaccharide is precipitated, as with three volumes of 99% IPA. The precipitate is dried for about three hours at about 60° C. (retained $H_2O$ less than 20%) and milled. If neutralization is omitted, the precipitated product is in the alkali metal salt form.

The process of this invention can also be used on other crude forms of tamarind where it is desired to enhance clarity, e.g., on tamarind splits, which are partially cracked tamarind seeds, or the cold-water soluble TKP described in U.S. Ser. No. 959,120, filed Nov. 9, 1978 and EPO Appln. 11, 951.

The clarified tamarind product of this invention can be used in applications where the crude TKP can be used, for example, in warp sizing (see Chem. Abstr. 45:8252 h and 47:326a), latex rubber (see Chem. Abstr. 42:2127b and 44:3277e), adhesives (see Chem. Abstr. 55:19237i; 64:17857c, and 69:60174u), in the paper and plywood industries (see Chem. Abstr. 52:5030b; 56:5004i; and 60:12226e), and in explosives (see Chem. Abstr. 55:25255b and 62:4654f). It is especially useful where clarity is required such as in replacing pectin. The clarified tamarind kernel powder of this invention can also be further purified to provide a thickener for products intended for human or animal consumption.

The invention is further defined by reference to the following examples which are intended to be illustrative and not limiting.

In the Examples, % transmittance (%T) in all cases were measured at 485 nm (vs. a water blank) using a Bausch and Lomb Spectronic 20 spectrophotometer.

EXAMPLE 1

PREPARATION OF CLARIFIED TAMARIND KERNEL POWDER

To 500 g of TKP (approximately 2 moles of polysaccharide) is added 480 g of a 50% NaOH aqueous solution (approximately 6 moles) in a Day mixer. ($NH_3$ vapors are immediately produced.) This is mixed for about 2 hours and then transferred to a Hobart mixer and 5 liters of $H_2O$ is added. After stirring for an additional 2 hours, the solution is placed in a cold room overnight. One half is neutralized with concentrated HCl and precipitated with 3 volumes IPA. The other half is likewise precipitated but without neutralization. The unneutralized precipitate is quite wet and so is slurried with methanol. Both precipitates are dried in a steam oven at about 60° C. for 3 hours. The neutralized product yields 226.4 g; the unneutralized 228.5 g. The data of Table 1 are obtained. Viscosities are obtained in D.I. water (or with added KCl) after stirring for 2 hours at room temperature.

TABLE 1

|  | Viscosity (cP)* | | | | % Trans. | |
|---|---|---|---|---|---|---|
|  | 1% D.I. | 1% D.I./ KCl | 2% D.I. | 2% D.I./ KCl | 1% D.I. | 2% D.I. |
| Clarified TKP |  |  |  |  |  |  |
| Neutralized | 20 | 18.3 | 141.5 | 125.5 | 49 | 215 |
| Un-neutral | 12.5 | 11.8 | 50 | 48 | 60 | 38 |

*Brookfield LVF viscometer, spindle 2, 60 rpm, 25° C.

EXAMPLE 2

ALKALI-CLARIFICATION OF TAMARIND SPLITS 500 g of hydrated tamarind splits, 240 ml of 50% NaOH aqueous solution, and 260 mls of D.I. water are placed in a Day Mixer and allowed to mix. After about 9.5 hours, a few small lumps remain and the rest appears well dissolved. The mixture is allowed to sit overnight. Then the mix is removed with 1500 ml D.I. water. The solution is neutralized with concentrated HCl and then precipitated with 4 volumes of methanol. 193.5 g of alkali-clarified tamarind are recovered. The data of Table 2 are obtained. Viscosities are obtained as in Example 1.

TABLE 2

|  | Viscosity (cP) | | % Trans. | |
|---|---|---|---|---|
|  | 1% D.I. | 2% D.I. | 1% D.I. | 2% D.I. |
| Alkali-clarified splits | 10.5 | 48.0 | 52 | 35 |

EXAMPLE 3

PREPARATIONS OF COLD-WATER SOLUBLE TKP

A cold-water soluble, dry form of crude TKP, described in U.S. Ser. No. 959,120, filed Nov. 9, 1978, now abandoned, is prepared.

Method 1

TKP is dispersed in water to a concentration of 20%, heated to 95° C. for 10 minutes, then dried and milled.

Method 2

TKP is dispersed in water at ambient temperature at a concentration of 40%. The resulting paste is drum dried with internal steam pressure at 40 psi, and then milled.

EXAMPLE 4

COMPARISON OF CLARIFIED TKP WITH OTHER TAMARIND PRODUCTS

The clarified tamarind product of Example 1 is compared with various other tamarind products: (1) the cold-water soluble form of TKP of Example 3; (2) tamarind kernel gum powder, prepared by milling tamarind seed kernels; (3) tamarind gellose, the purified tamarind polysaccharide available commercially as Glyloid 3A and 3S (Sancho Co., Ltd., Osaka, Japan). Glyloid 3A is described as a cold-dispersible product which requires heating at 70° C. for 15 minutes to obtain maximum viscosity. Glyloid 3S is a cold-water soluble product. Both are food grade products. The data of Table 3 are obtained. In the table, %N was calculated via the Kjeldahl method; % protein = % N × 6.25.

TABLE 3

| Sample | % N | % Protein | % T (0.25%) | % T (1%) | Viscosity (cP)* | | 1% D.I./ 1% KCl |
|---|---|---|---|---|---|---|---|
|  |  |  |  |  | 1% D.I. | 2% D.I. |  |
| 1. Clarified TKP, un-neut. | 0.35 | 2.20 | 77 | 60 | 12.5 | 50 | 12 |
| 2. Clarified TKP, neut. | 1.32 | 8.24 | 72 | 49 | 20 | 142 | 18 |
| 3. CWS-TKP (Examp. 3) | 3.20 | 19.97 | 11 | 2 | 41 | 462 | 46 |
| 4. Tam. kernel powder | 2.17 | 13.55 | 9 | 0 | 5 | 6 | 4 |
| 5. Gly. - 3A | 0.28 | 1.72 | 93 | — | — | — | — |
| 6. Gly. - 3S | 0.04 | 0.26 | 94 | — | — | — | — |

*Brookfield LVT viscometer, spindles 1 and 2, 60 rpm, 25° C., measured in D.I. water (or with added KCl) after stirring for 2 hrs. at room temperature.

What is claimed is:

1. A process for preparing clarified tamarind kernel powder which comprises preparing an aqueous slurry of TKP and a strong alkali, mixing said slurry, then optionally neutralizing said slurry, and isolating said clarified tamarind kernel powder.

2. The process of claim 1, wherein the pH of the aqueous slurry ranges from about pH 10 to about pH 14, the alkali is NaOH, and the powder is isolated by precipitation with lower alkyl alcohol.

3. The process of claim 2, wherein the pH of the slurry is about pH 13.

4. The process of claim 3, wherein the slurry is mixed for about four hours.

5. The process of claim 4, which comprises preparing an aqueous slurry of TKP and an equal weight of a 50% NaOH aqueous solution and diluting said slurry with about five volumes of water.

6. The process of claim 5, wherein after mixing the slurry, the slurry is neutralized with HCl.

7. Clarified tamarind kernel powder prepared by the process of claim 1 comprising about 2–10 wt.% protein, characterized in that a 0.25% deionized water solution exhibits 70–80% transmittance at 485 nm using a Bausch and Lomb Spectronic 20 spectrophotometer standardized against a water blank.

8. The powder of claim 7, comprising less than 2% $H_2O$.

9. The alkali metal salt of the powder of claim 8.

10. The salt of claim 9, comprising about 2.2% protein, characterized in that a 0.25% deionized water solution exhibits 70–80% transmittance at 485 nm.

* * * * *